US008647858B2

(12) United States Patent
Broyer et al.

(10) Patent No.: US 8,647,858 B2
(45) Date of Patent: Feb. 11, 2014

(54) AUTOMATED SYSTEM FOR THE LYSIS OF MICROORGANISMS PRESENT IN A SAMPLE, FOR EXTRACTION AND FOR PURIFICATION OF THE NUCLEIC ACIDS OF SAID MICROORGANISMS FOR PURPOSES OF ANALYSIS

(75) Inventors: Patrick Broyer, Saint-Cassien (FR); Agnes Dupontfilliard, Les Adrets (FR); Massimo Galdiero, San Casciano Val di Pesa-Firenze (IT); Michel Guy, Grenoble (FR); Hermanus Johannes Maria Kreuwel, Schijndel (NL); Emiliano Maione, Bagno a Ripoli (IT); Emiel Gerebern Maria Verwimp, Kasterlee (BE)

(73) Assignee: Biomerieux, Marcy l'Etoile (FR)

( * ) Notice: Subject to any disclaimer, the term of this patent is extended or adjusted under 35 U.S.C. 154(b) by 43 days.

(21) Appl. No.: 13/129,997

(22) PCT Filed: Dec. 9, 2009

(86) PCT No.: PCT/FR2009/052458
§ 371 (c)(1),
(2), (4) Date: May 18, 2011

(87) PCT Pub. No.: WO2010/067019
PCT Pub. Date: Jun. 17, 2010

(65) Prior Publication Data
US 2011/0250680 A1 Oct. 13, 2011

(51) Int. Cl.
*C12M 1/34* (2006.01)
*C12M 3/00* (2006.01)
*C12Q 1/68* (2006.01)
*C12P 19/34* (2006.01)
*G01N 15/06* (2006.01)
*G01N 33/00* (2006.01)
*G01N 33/48* (2006.01)

(52) U.S. Cl.
USPC ....... 435/287.1; 435/6.1; 435/6.11; 435/91.1; 435/287.2; 422/68.1

(58) Field of Classification Search
USPC ........... 435/6.1, 6.11, 7.1, 40.5, 283.1, 287.1, 435/287.2, 6.15; 422/50, 68.1
See application file for complete search history.

(56) References Cited

U.S. PATENT DOCUMENTS

| | | | | |
|---|---|---|---|---|
| 3,831,621 | A * | 8/1974 | Anthony et al. | 137/270 |
| 4,672,040 | A | 6/1987 | Josephson | |
| 5,567,050 | A | 10/1996 | Zlobinsky et al. | |
| 5,707,861 | A | 1/1998 | Sherman et al. | |
| 5,750,338 | A | 5/1998 | Collins et al. | |
| 6,398,402 | B1 | 6/2002 | Thomas et al. | |
| 6,632,662 | B1 | 10/2003 | Broyer et al. | |
| 2002/0185557 | A1 | 12/2002 | Sparks | |
| 2004/0038385 | A1 | 2/2004 | Langlois et al. | |
| 2005/0070944 | A1 | 3/2005 | Holl et al. | |
| 2005/0191620 | A1 * | 9/2005 | McDevitt et al. | 435/5 |
| 2007/0015177 | A1 | 1/2007 | Maron et al. | |
| 2007/0064521 | A1 | 3/2007 | Miszenti | |
| 2007/0068284 | A1 | 3/2007 | Castro et al. | |

FOREIGN PATENT DOCUMENTS

| | | | |
|---|---|---|---|
| EP | 0 303 791 | A1 | 2/1989 |
| FR | 2 607 507 | A1 | 6/1988 |
| FR | 2 781 500 | A1 | 1/2000 |
| FR | 2 781 802 | A1 | 2/2000 |
| FR | 2 861 085 | A1 | 4/2005 |
| GB | 203402 | | 9/1923 |
| GB | 2 254 024 | A | 9/1992 |
| WO | WO 95/08000 | A2 | 3/1995 |
| WO | WO 97/45202 | A1 | 12/1997 |
| WO | WO 99/35500 | A1 | 7/1999 |
| WO | WO 00/73412 | A2 | 12/2000 |
| WO | WO 2004/018704 | A2 | 3/2004 |
| WO | WO 2005/038025 | A1 | 4/2005 |
| WO | WO 2006/117676 | A2 | 11/2006 |
| WO | WO 2008/104916 | A2 | 9/2008 |

OTHER PUBLICATIONS

Boom et al., "Rapid and Simple Method for Purification of Nucleic Acids," *Journal of Clinical Microbiology*, 1990, vol. 28, No. 3, pp. 495-503.
Levison et al., "New approaches to the isolation of DNA by ion-exchange chromatography," *Journal of Chromatography A*, 1998, vol. 827, pp. 337-344.
Kumar et al., "The First Analogues of LNA (Locked Nucleic Acids): Phosphorothioate-LNA and 2'-Thio-LNA," *Bioorganic & Medicinal Chemistry Letters*, 1998, vol. 8, pp. 2219-2222.

(Continued)

*Primary Examiner* — Frank Lu
(74) *Attorney, Agent, or Firm* — Oliff PLC

(57) ABSTRACT

The present invention relates to, among other things, a device for collecting airborne microorganisms, said device having:
an air collecting module, comprising:

i. an upper element having an air admission duct permitting entry of an air stream into said module, said duct being provided, at its base, with means for disturbance of the air stream, ii. a lower element having air evacuating means permitting the air stream created to exit and said upper and lower elements can be made integral with one another so that the air stream can be created within said air collecting module;

a cartridge, of roughly cylindrical shape, having a microorganism retention zone, said retention zone having means for lysis of the microorganisms, said cartridge being positioned within said air collecting module.

10 Claims, 7 Drawing Sheets

(56) References Cited

OTHER PUBLICATIONS

Egholm et al., "Peptide Nucleic Acids (PNA). Oligonucleotide Analogues with an Achiral Peptide Backbone," *J. Am. Chem. Soc.*, 1992, vol. 114, pp. 1895-1897.

Chevalier et al., "Biotin and Digoxigenin as Labels for Light and Electron Microscopy in Situ Hybridization Probes: Where Do We Stand?," *The Journal of Histochemistry & Cytochemistry*, 1997, vol. 45, No. 4, pp. 481-491.

International Search Report in International Application No. PCT/FR2009/052458; Aug. 9, 2010 (with English-language translation).

Written Opinion of the International Searching Authority in International Application No. PCT/FR2009/052458; Aug. 9, 2010 (with English-language translation).

Feb. 25, 2009 International Search Report issued in International Patent Application No. PCT/FR2008/051012.

U.S. Appl. No. 12/451,486, filed Nov. 13, 2009, in the name of Kreuwel et al.

Jun. 15, 2012 Office Action issued in U.S. Appl. No. 12/451,486.

* cited by examiner

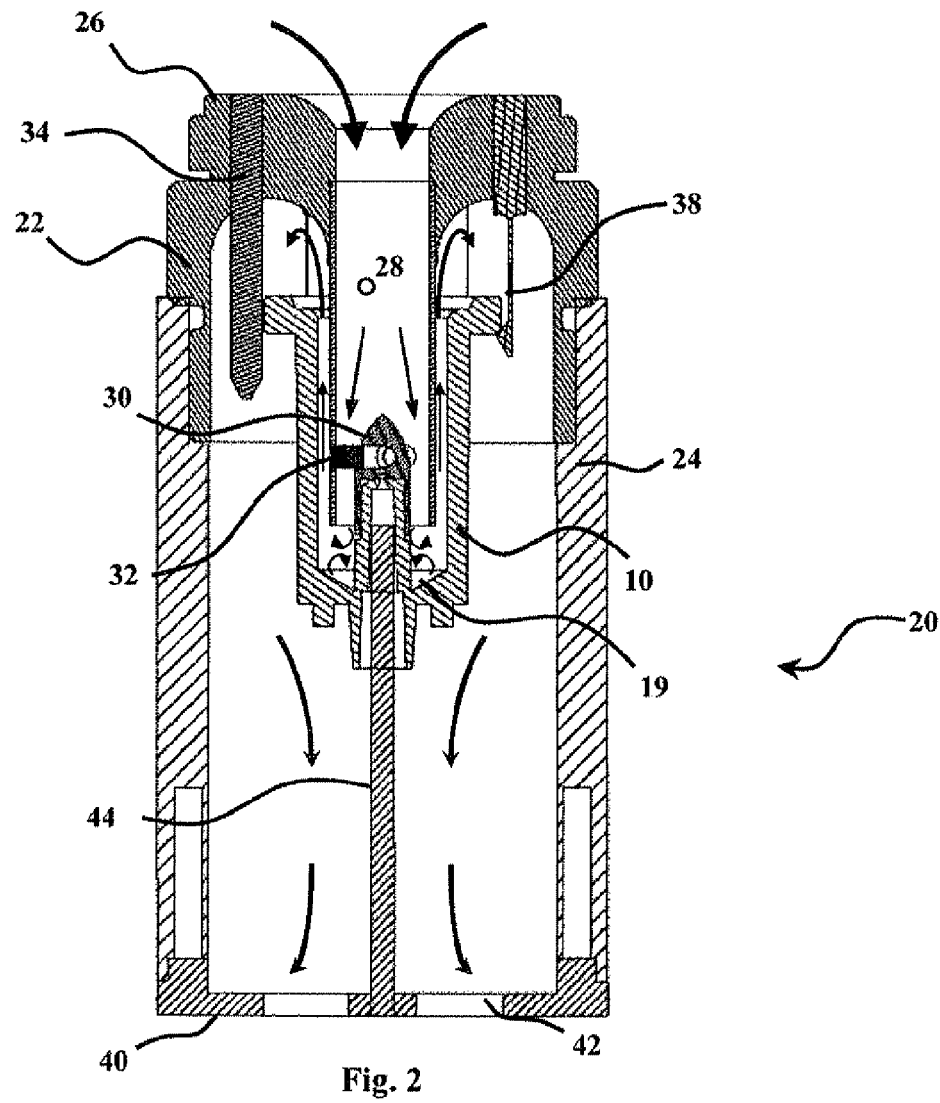
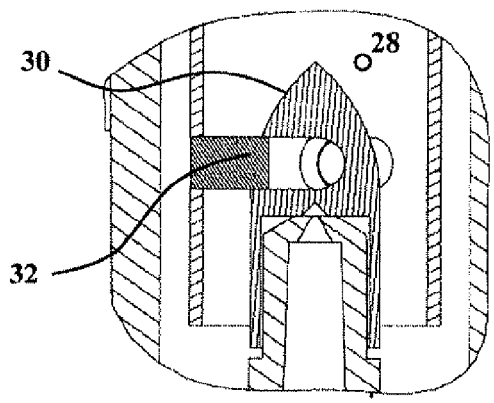
Fig. 2
Fig. 3

AUTOMATED SYSTEM FOR THE LYSIS OF MICROORGANISMS PRESENT IN A SAMPLE, FOR EXTRACTION AND FOR PURIFICATION OF THE NUCLEIC ACIDS OF SAID MICROORGANISMS FOR PURPOSES OF ANALYSIS

BACKGROUND

The technical field of the present invention is that of biological analysis. More particularly, the present invention relates firstly to a device for lysis of microorganisms present in an environmental or clinical sample, for extraction and for purification of the nucleic acids of said microorganisms. The invention further relates to an automated system for lysis of the microorganisms, for extraction and for purification of the nucleic acids of said microorganisms, for purposes of analysis.

An upsurge in nosocomial infections in hospitals has been observed for several years. These infections are explained by contamination of hospitalized, and therefore by definition immunodepressed, persons by pathogenic microorganisms present in the hospital environment and not destroyed despite considerable care always being applied to the disinfection of equipment and surfaces and to air treatment. In view of these more and more frequent cases of environmental microbiological contamination, the development of devices and methods for improving and facilitating environmental controls has become a major challenge for health professionals.

In addition to the problem of nosocomial infections, control of environmental conditions has also been a recurrent concern in industry for many years, in particular in food industries, and pharmaceutical or cosmetic industries. In food industries, the disastrous consequences for consumers' health that can arise from contamination of products, or even of raw materials, by a pathogenic microorganism are well known. In fact, food poisoning due to bacteria such as those of the genus *Listeria* or *Salmonella* is now a common occurrence. Control of air quality is also a key process in the quality approach of pharmaceutical or cosmetic industries.

Moreover, these controls must comply with ever increasing requirements, as regulations become stricter all the time.

Among the tools at the disposal of health professionals or manufacturers for carrying out environmental controls, microbiological air samplers are solutions of choice for the detection of airborne microorganisms. These devices are placed at suitable points in places where measurement of microbiological air contamination is required. They are generally constituted of an air sampler coupled to a culture medium. The air collected by the air sampler comes into contact with the culture medium; any microorganisms contained in the air collected will be deposited on the culture medium. The culture medium is then recovered and placed in a stove to promote growth of the microorganisms. It is thus possible to detect and identify said microorganisms by conventional microbiological techniques.

These devices nevertheless have a major drawback, which is connected with the technology used. This drawback is the time taken to obtain the analysis result. In fact, the use of conventional techniques of microbiology, in particular of bacteriology, requires incubation times necessary for cell growth, or even phases of re-seeding on specific culture media to permit identification. As a result, the time taken to obtain a result is relatively long, or even too long, when we are trying to detect and identify a pathogen that is responsible for a nosocomial infection or for food poisoning.

Another drawback of a device of this type is that although the use of culture media makes it possible to discriminate between genera and species of bacteria, generally it does not allow discrimination of the strains of one and the same bacterial species. Now, it is known that the pathogenicity of a microorganism can vary significantly depending on the strain in question.

Moreover, this type of device has the drawback that it is unable to detect airborne microorganisms that are viable but cannot be cultured.

There are, moreover, devices intended for recovery of airborne particles, in particular microorganisms. Thus, document GB-2 254 024 describes a device for collecting airborne particles whose principle is based on the cyclone effect. Although such a device is found to be suitable for collecting airborne particles, including microorganisms, it has never been investigated for treating the sample thus obtained, in particular for extracting genetic material intended to be used for analysis.

More generally, the techniques that are most relevant in terms of identification of microorganisms and/or of speed of delivering the results, whether with respect to clinical or environmental samples, are undoubtedly the techniques of molecular diagnostics. These techniques, based on analysis of the genetic material of the microorganisms, and in particular of certain specific sequences of interest, make it possible to obtain a very precise identification of microorganisms in record time, since they make it possible to omit the culture steps.

Nevertheless, the use of such techniques has certain limits, the most important of which is the potentially limited quantity of microorganisms that are present in the air and therefore recoverable for performing the analysis. In fact, it is known that environmental samples, as well as certain clinical samples, are relatively poor in microorganisms. Consequently, only a small amount of genetic material is obtained from this raw material. The performance of the technique used for extracting the nucleic acids, in terms of yield, then becomes a crucial parameter.

Moreover, most of the existing techniques for lysis of microorganisms are not of general application for all microorganisms and/or require the intervention of qualified personnel for taking care of the manual stages.

Document WO-A-2005/038025 describes a method for extracting nucleic acids from microorganisms, notably from air samples. This method comprises the use of three different methods of lysis, namely chemical lysis, lysis by thermal shock and mechanical lysis. Although such a method undoubtedly makes it possible to optimize the efficiency of extraction of the nucleic acids and therefore to increase the amount of genetic material available for analysis, this efficiency still depends on the quantity of microorganisms recovered. Yet, nothing is described in that document for optimizing the recovery of said microorganisms.

Document U.S. Pat. No. 5,707,861 describes a device for disrupting living cells such as microorganisms. This device makes it possible to lyse the cells by utilizing glass beads, but in addition by the effect of vibration due to the gap that exists between the tubes containing the microorganisms and the holes in the support holding said tubes. Thus, a device of this kind makes it possible to optimize cell lysis and therefore optimize extraction of the genetic material. Said device and the method employed by the latter have the same limitations as those mentioned above, namely they still depend on the quantity of microorganisms recovered. Moreover, they have the additional drawback of requiring a subsequent stage of concentration of the nucleic acids in order to isolate them from the cellular debris. Finally, they require manual recovery of the nucleic acids, at the end of the concentration stage.

These problems also arise with the device described in document U.S. Pat. No. 5,567,050.

Systems that are more integrated have also been described. Thus, document WO-A-2004/018704 describes a device, and an associated method using the PCR (Polymerase Chain Reaction) amplification technique, for collecting microorganisms from the air and identifying them. This system is particularly suitable for combating attempted attacks by biological contamination in postal sorting centers. This system is composed of an air sampler positioned along the circuit for transporting the mail, a device for filtration/separation of particles by the cyclone effect, a device for concentration/recovery of the particles in a liquid sample, and a device for transferring a fraction of the sample to a GeneXpert™ PCR analysis cartridge from the company Cepheid. The cartridge is then transferred manually to a separate automatic biological analyzer for identification of the microorganism or microorganisms collected from the air.

Although this system makes it possible to solve a great many of the technical problems associated with the devices and methods described above, it nevertheless has some major drawbacks. The first of these drawbacks is that the system for treatment of the sample (collection, separation, concentration/recovery) prior to transfer to the analysis cartridge is relatively complex and expensive. Another drawback is that there is no GeneXpert™ cartridge that can perform both lysis and purification of nucleic acids. Yet a second drawback is that the microorganisms collected are recovered in a liquid sample, only a fraction of which is analyzed. This means that the risk of not recovering all of the microorganisms and therefore all of the nucleic acids is very high, greatly restricting the relevance of the analysis. Moreover, despite its complexity, this system requires manual transfer of the cartridge to the GeneXpert™ automatic analyzer.

Thus, a first aim of the present invention is to provide a device, a system and a universal method of lysis, which are effective both for environmental and clinical samples, for a great variety of microorganisms, whether they are bacteria, viruses or fungi, optionally in the vegetative state or in the form of spores.

Another aim of the present invention is to provide a device suitable for efficiently lysing said microorganisms contained in an environmental sample such as air, or in a clinical sample, in order to extract the nucleic acids from it and recover said nucleic acids for the purpose of analysis, in an integrated manner.

Another aim of the present invention is to provide a device suitable for collecting all of the microorganisms contained in an air sample.

Another aim of the present invention is to provide a device of simple design, minimizing the number and the complexity of the manual stages.

Another aim of the present invention is to provide a device that is extremely compact.

Another aim of the present invention is to provide a closed device in which the various stages enumerated above take place without risk of external contamination.

Another aim of the present invention is to provide a device in which said stages take place without transfer of the sample by the operator, thus preventing contamination of the latter.

Another aim of the present invention is to provide a device and a system that limits human intervention and improves the traceability of sample treatment.

Finally, another aim of the present invention is to provide a device and an automated system capable of supplying target nucleic acids in a buffer that can be used directly in stages of molecular diagnostics comprising for example stages of amplification and of detection, without additional stages of pretreatment such as centrifugation or filtration.

BRIEF SUMMARY

These aims, among others, are achieved by the present invention, which relates, firstly, to a device for collecting airborne microorganisms, said device having:
  an air collecting module, comprising:
    i. an upper element having an air admission duct permitting entry of an air stream into said module, said duct being provided, at its base, with means for disturbance of the air stream,
    ii. a lower element having means for evacuation of the air, permitting exit of the air stream created
    and said upper and lower elements can be made integral with one another so that the air stream can be created within said air collecting module;
  a cartridge, of roughly cylindrical shape, having a microorganism retention zone, said retention zone having means for lysis of the microorganisms, said cartridge being positioned within said air collecting module.

Preferably, the microorganism retention zone of the cartridge of the microorganism collecting device further comprises a material that is able to retain the microorganisms, to hold the means for lysis in place and to be dissolved in the presence of a liquid.

In the device according to the invention, the means for disturbance of the air stream comprises a cone of ogive shape positioned at the center of the bore of the air admission duct and at least one blade connecting said ogive-shaped piece to the inside surface of the air admission duct.

Advantageously, the air collecting module is intended to be connected to a circuit for recycling the air or to a device for aspiration of the air.

The present invention also relates to a device for lysis of microorganisms, said device having:
  a cartridge, of roughly cylindrical shape, having a retention zone for the microorganisms, said cartridge performing the role of stator;
  a rotor, which can be placed in the cartridge, said rotor having means for rotation.

According to a preferred embodiment, this device further comprises a cap intended for keeping the rotor integral with the cartridge.

Advantageously, the rotating means are constituted of grooves made in the wall of a blind duct, said grooves being diametrically opposite and intended to receive the end of a transmission shaft of the means for rotating said rotor.

According to a noteworthy characteristic of this device for lysis of microorganisms, the inside diameter of the cartridge is greater than the outside diameter of the rotor, so that when the rotor is fitted in the cartridge, the distance separating the inside wall of the cartridge from the outside wall of the rotor is large enough to permit the means for lysis to be positioned in this interstitial space and small enough for the means for lysis to be in contact with one or other of said walls.

The present invention further relates to a system for lysis of microorganisms and for purification of the nucleic acids of said microorganisms, having:
  means for positioning the device for lysis of microorganisms according to the invention;
  means for rotating the rotor, when the device for lysis is placed on the positioning means;
  at least one container for receiving nucleic acids;

at least one means for aspiration/discharge of liquid;

a multi-way valve, in fluidic communication with the device for lysis of microorganisms, container for receiving purified nucleic acids and means for aspiration/discharge of liquid.

Preferably, this lysis system according to the preceding claim further comprises means for magnetization. It can also comprise heating means.

According to a particular embodiment of the invention, the multi-way valve comprises aspiration-expulsion means.

The invention also relates to a method of collecting airborne microorganisms, said method comprising stages consisting of:
 a) placing a cartridge inside an air collecting module, so as to obtain the microorganism collecting device according to the invention, the retention zone within said cartridge being in communication with the air admission duct of the air collecting module,
 b) causing air to go into said air collecting module by any suitable means,
 c) collecting the airborne microorganisms in the retention zone of the cartridge.

The invention also relates to a method of lysis of airborne microorganisms, said method having stages consisting of:
 a) placing a cartridge inside an air collecting module, so as to obtain the microorganism collecting device according to the invention, the retention zone within said cartridge being in communication with the air admission duet of the air collecting module,
 b) causing air to go into said air collecting module by any suitable means,
 c) collecting the airborne microorganisms in the retention zone of the cartridge,
 d) removing the cartridge from the air collecting module,
 e) placing the rotor in the cartridge, so as to obtain the device for lysis of Microorganisms,
 positioning the device for lysis of microorganisms in the system for lysis of microorganisms and purification of nucleic acids,
 g) introducing an elution liquid into the cartridge, for suspending the lysis means situated in the microorganism retention zone of the cartridge, and
 h) mechanically lysing the microorganisms, by rotating the rotor within the cartridge by the rotating means of said rotor, said rotor causing the means for lysis of microorganisms to rotate.

"Elution liquid" means any liquid suitable for permitting lysis, or even extraction and recovery of the nucleic acids in good condition. Said liquid is generally a buffer. In the case when application of the method according to the invention is for the purpose of extracting the nucleic acids and recovering them for purposes of analysis, said buffer is to permit conservation of said nucleic acids. Liquids of this kind are well known by a person skilled in the art.

The invention also relates to a method of extracting the nucleic acids from airborne microorganisms, said method having stages consisting of:
 a) placing a cartridge inside an air collecting module, so as to obtain the microorganism collecting device according to the invention, the retention zone within said cartridge being in communication with the air admission duct of the air collecting module,
 b) causing air to go into said air collecting module by any suitable means,
 c) collecting the airborne microorganisms in the retention zone of the cartridge,
 d) removing the cartridge from the air collecting module,
 e) placing the rotor in the cartridge,
 f) introducing an elution liquid into the cartridge by aspiration-discharge means, for suspending the lysis means contained in the cartridge, and
 g) mechanically lysing the microorganisms, by rotating the rotor within the cartridge by the rotating means of said rotor, said rotor causing the lysis means to rotate, and
 h) aspirating the elution liquid containing the nucleic acids of said microorganisms released during lysis, and
 i) dispensing the elution liquid in a container for receiving and purification of the nucleic acids.

Preferably, the methods of lysis of microorganisms and extraction of nucleic acids described above comprise an additional stage d') consisting of growing the microorganisms concentrated in the retention zone of the cartridge.

Advantageously, growing is achieved by incubation of the cartridge in a stove for a time in the range from 2 to 24 hours.

Preferably, stages f) to i) of the methods of lysis of microorganisms and extraction of nucleic acids described above are applied in the system for lysis of microorganisms and purification of nucleic acids.

The invention also relates to a method of lysis of microorganisms, said method having stages consisting of:
 a) obtaining a cartridge in which microorganisms are concentrated in the retention zone of said cartridge,
 b) placing the rotor in the cartridge,
 c) introducing a liquid of interest into the cartridge, for suspending the lysis means situated in the microorganism retention zone of the cartridge, and
 d) mechanically lysing the microorganisms, by rotating the rotor within the cartridge, said rotor causing the means for lysis of microorganisms to rotate.

The invention also relates to a method of extracting the nucleic acids from microorganisms, said method having stages consisting of
 a) obtaining a cartridge in which microorganisms are concentrated in the retention zone,
 b) placing the rotor in the cartridge,
 c) introducing an elution liquid into the cartridge, for suspending the lysis means situated in the microorganism retention zone of the cartridge, and
 d) mechanically lysing the microorganisms, by rotating the rotor within the cartridge, said rotor causing the means for lysis of microorganisms to rotate, and
 e) aspirating the elution liquid containing the nucleic acids of said microorganisms released during lysis, and
 f) dispensing the elution liquid in a container for receiving and purification of the nucleic acids.

The present invention further relates to a method of lysis of microorganisms contained in a liquid sample, said method having stages consisting of:
 a) introducing the liquid sample containing said microorganisms into a cartridge, in the vicinity of the retention zone, so that said liquid sample leads to suspending of the lysis means situated in said microorganism retention zone of the cartridge,
 b) placing the rotor in the cartridge,
 c) mechanically lysing the microorganisms, by rotating the rotor within the cartridge, said rotation leading to the suspending of the lysis means situated in said microorganism retention zone of the cartridge, said rotor causing the lysis means, on which the microorganisms are retained, to rotate.

"Liquid sample" means any liquid sample that may contain microorganisms. It can be a liquid sample of human or animal origin. Said sample can be, for example, urine, whole blood, plasma or any other body fluid. The liquid sample can be of food origin, such as a drink. It can also be of environmental origin, such as water. Moreover, the liquid sample can also be a so-called transfer liquid, in which any microorganisms present on a surface sampling device, of the swab type such as those marketed by the company COPAN, under the name flockedSWABS, have been resuspended by agitation of said swab in said transfer liquid.

The invention also relates to a method of extracting the nucleic acids from microorganisms contained in a liquid sample, said method having stages consisting of
a) introducing a liquid sample containing said microorganisms into a cartridge in the vicinity of the retention zone, so that said liquid sample leads to suspending of the lysis means situated in said microorganism retention zone of the cartridge,
b) placing the rotor in the cartridge,
c) mechanically lysing the microorganisms, by rotating the rotor within the cartridge, said rotation leading to suspending of the lysis means situated in said microorganism retention zone of said cartridge, said rotor causing the lysis means, on which the microorganisms are retained, to rotate,
d) aspirating the liquid sample containing the nucleic acids of said microorganisms released during lysis and
e) dispensing the liquid sample in a container for receiving the nucleic acids.

The present invention further relates to a method of extraction of the nucleic acids of a sample of cellular tissue, said method having stages consisting of:
a) introducing the sample of cellular tissue into the cartridge in the presence of an elution liquid,
b) placing the rotor in the cartridge,
c) mechanically lysing the cells of the cellular tissue, by rotating the rotor within the cartridge, said rotor causing the lysis means contained in the cartridge to rotate,
d) aspirating the elution liquid containing the nucleic acids of said cells, released during lysis and
e) dispensing the elution liquid in a container for receiving nucleic acids.

"Tissue sample" means any tissue sample of human or animal origin from which it is possible to extract nucleic acids. Such a sample can be obtained by biopsy for example of an organ, of a muscle, or of skin. These tissues can be healthy or pathological, notably tumoral.

It should be noted that all the methods of extraction of nucleic acids according to the invention can have, according to an advantageous embodiment, an additional purification stage of these nucleic acids, with a view to a subsequent treatment such as an amplification. This purification stage permits separation between the nucleic acids and the other cellular constituents salted-out in the lysis stage. This stage generally makes it possible to concentrate nucleic acids, and can be adapted to the purification of DNA or of RNA. It can be performed by means of magnetic particles. As an example, it is possible to use magnetic particles optionally coated with oligonucleotides, by adsorption or covalent bonding (cf. patents U.S. Pat. Nos. 4,672,040 and 5,750,338), and thus purify the nucleic acids that have adhered to these magnetic particles by a washing stage. This stage for purification of nucleic acids is particularly useful if subsequent amplification of said nucleic acids is required. A particularly interesting embodiment of these magnetic particles is described in patent applications WO-A-97/45202 and WO-A-99/35500. Another interesting example of a method of purification of nucleic acids is the use of silica either in the form of a column, or in the form of inert particles (Boom R. et al., J. Clin. Microbial., 1990, No. 28(3), p. 495-503) or magnetic particles (Merck: MagPrep® Silica, Promega: MagneSil™ Paramagnetic particles). Other widely used methods are based on ion exchange resins in a column or in paramagnetic particle format (Whatman: DEAE-Magarose) (Levison PR et al., J. Chromatography, 1998, p. 337-344). Another method that is very pertinent but not exclusive for the invention is adsorption on a metal oxide support (from the company Xtrana: Xtra-Bind™ matrix).

Moreover, in the various methods described above, all the stages subsequent to reconstitution of the device for lysis of microorganisms, i.e. once the rotor is placed in the cartridge, can advantageously be employed in the system for lysis of microorganisms and purification of nucleic acids.

The present invention further relates to the use of the device for lysis of microorganisms according to the invention for lysis of the cells of a sample of cellular tissue.

The present invention further relates to the use of the system for lysis of microorganisms and purification of the nucleic acids of said microorganisms according to the invention, for lysis of the cells of a sample of cellular tissue and purification of the nucleic acids of said cells for purposes of analysis.

The microorganisms are taken from the group comprising bacteria, viruses, yeasts, molds, and parasites.

The samples from which the microorganisms are isolated are of environmental origin. Thus, it can be a sample of air or of liquid, such as water; or surface samples. The samples can also be of clinical origin, i.e. any sample of human or animal origin, which can be the object of an analysis for detecting and identifying a microorganism, optionally pathogenic.

The presence of the target nucleic acids can be demonstrated by visualization of hybridization reactions. Hybridization reaction means any reaction between a captured nucleic acid and a target nucleic acid isolated or generated by a stage of transcription, of reverse transcription or of amplification of the NASBA (Nucleic Acid Sequence Based Amplification) type or PCR (Polymerase Chain Reaction).

Nucleic acid means oligonucleotides, deoxyribonucleic acids and ribonucleic acids, as well as their derivatives. The term oligonucleotide denotes a sequence of at least two nucleotides (deoxyribonucleotides or ribonucleotides, or both), natural or modified, capable of hybridizing, in suitable hybridization conditions, to an oligonucleotide that is at least partially complementary. Modified nucleotide means for example a nucleotide having a modified base and/or having a modification in the internucleotide bond and/or in the backbone. As an example of a modified base, we may mention inosine, methyl-5-deoxycytidine, dimethylamino-5-deoxyuridine, diamino-2,6-purine and bromo-5-deoxyuridine.

To illustrate a modified internucleotide bond, we may mention the phosphorothioate, N-alkylphosphoramidate, alkylphosphonate and alkylphosphodiester bonds.

The alpha-oligonucleotides such as those described in FR-A-2 607 507, the LNAs such as phosphorothioate-LNA and 2'-thio-LNA described in Bioorganic & Medicinal Chemistry Letters, Volume 8, Issue 16, 18 Aug. 1998, pages 2219-2222, and the PNAs discussed in the article of M. Egholm et al., J. Am. Chem. Soc. (1992), 114, 1895-1897, are examples of oligonucleotides constituted of nucleotides with a modified backbone.

The hybridization reactions can be visualized by any means of detection, such as direct or indirect means.

In the case of direct detection, i.e. without the use of labeling, hybridization reactions are observed by plasmon resonance or by cyclic voltammetry on an electrode carrying a conducting polymer.

In the case of indirect detection, i.e. by means of labeling, the labeling can be performed either directly on the target nucleic acids, or via a specific binding partner of said nucleic acids that was labeled beforehand.

Specific binding partner of the target nucleic acids means any partner capable of binding to the target nucleic acid, and as examples we may mention nucleic acids, oligonucleotides or polynucleotides and enzyme substrates.

"Labeling" means attaching a marker capable of generating, directly or indirectly, a detectable signal. A nonexhaustive list of these markers comprises: enzymes that produce a signal that is detectable for example by electrochemistry, colorimetry, fluorescence, luminescence, enzymes such as horseradish peroxidase (HRP), alkaline phosphatase (ALP), α-galactosidase, glucose-6-phosphate dehydrogenase; enzyme inhibitors; enzyme co-factors; particles such as gold particles, magnetic latexes, liposomes; chromophores such as luminescent compounds, dyes, radioactive molecules such as $^{32}P$, $^{35}S$ or $^{125}I$, fluorescent molecules such as fluorescein, rhodamine, Alexa®, umbelliferone, luminol or phycocyanins. In the case of fluorescence, it can be the fluorescent product of an enzyme-substrate reaction, a fluorophore-quencher combination, extinction of fluorescence or any other system based on properties of fluorescence.

Indirect systems can also be used, for example via another ligand/antiligand pair. Ligand/antiligand pairs are well known by a person skilled in the art, and we may mention for example the following pairs: biotinlstreptavidin, sugar/lectin, polynucleotide/complementary polynucleotide. In this case, it is the ligand that carries the binding agent. The antiligand can be detectable directly by the markers described in the preceding paragraph or can itself be detectable by a ligand/antiligand.

These indirect detection systems can lead, in certain conditions, to amplification of the signal. This technique of signal amplification is well known by a person skilled in the art, and reference may be made to the applicant's previous patent applications FR-A-2 781 802 or WO-A-95/08000 or to the article J. Histochem. Cytochem. 45: 481-491, 1997.

The target nucleic acids can be labeled beforehand by direct or indirect incorporation of a marker by a polymerase, by a kinase, randomly or specifically, at the ends or by incorporation "within" the molecule.

Labeling of the specific binding partners of the target analytes is broadly known by a person skilled in the art and is described for example by Greg T. Hermanson in Bioconjugate Techniques, 1996, Academic Press Inc, 525B Street, San Diego, Calif. 92101 USA.

Depending on the type of labeling of the conjugate used, for example using an enzyme, a person skilled in the art will add reagents permitting visualization of the labeling. This stage corresponds to detection. It is preceded by the use of a washing buffer for removing the fractions of analytes or of elements not involved in the reaction, or bound weakly or nonspecifically, in order to limit background noise.

BRIEF DESCRIPTION OF THE DRAWINGS

The aims and advantages of the device according to the present invention will be better understood from the example given below, which is not in any way limiting, referring to the drawings, in which:

FIG. 2 shows a view in longitudinal section of the device for collecting airborne microorganisms, according to a particular embodiment.

FIG. 3 shows an enlarged partial view in longitudinal section of the microorganism collecting device as shown in FIG. 1.

DETAILED DESCRIPTION

Figure 1:
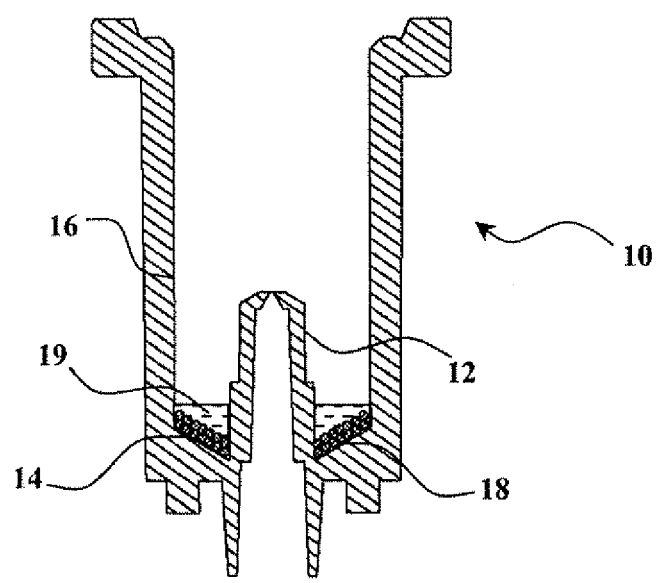
FIG. 1 shows a view in longitudinal section of the cartridge used for collection and lysis of the microorganisms.

A cartridge 10, shown in longitudinal section in FIG. 1, has the general shape of a cylinder of roughly circular cross section. The top end of the cylinder is free, whereas the bottom end is constituted of a wall, with a hole at its center, in the extension of which there is a duct 12 extending into the cartridge 10. It can be seen that the internal section of the duct tends to decrease as its top end is approached.

As can be seen in FIG. 1, the inside surface of the bottom wall 14 of the cartridge 10 is inclined, the lowest point of the slope being located where it makes contact with the duct 12 and the highest point being at the contact with the vertical wall 16 of the cartridge 10. This wall 14 serves as a support for the lysis means 18 and constitutes the microorganism retention zone. These lysis means are constituted in this case of beads of identical size, According to a preferred embodiment, these beads are of glass. They could, however, be constituted of any other equivalent material, such as iron. These beads advantageously have a diameter between 200 and 800 micrometers (µm).

According to an advantageous embodiment, the beads can be of different sizes. Thus, it may be particularly appropriate to use a mixture of beads with diameter between 200 and 300 µm with beads whose diameter is between 400 and 600 µm. Such beads are marketed for example by the company SIGMA under the reference Acid-washed glass beads, 425-600 µm, Ref: G8772.

The beads are held in place in the form of one or more superposed layers by means of a layer of jellified material 19, preferably disposed on the beads. The jellified material must meet several requirements. The first is that it must be inert, so as not to influence the procedures that are employed within the cartridge. The second is that it must have the capacity of dissolving in a liquid, for the application of lysis of microorganisms. Said material can for example be an agarose gel (Sigma Aldrich, Agarose—Type I-B Low EEO, Ref.: A0576-25G). The jellified material can also contain glycerol.

Alternatively, the jellified material can advantageously be a culture medium for microorganisms. In fact, agar culture media have long been used conventionally in the field of in-vitro diagnostics. The use of said culture medium offers several advantages. The main advantage is that it permits a phase of growth of the microorganisms before carrying out their lysis. Even if the device according to the invention aims to meet a need connected with rapid detection of pathogenic microorganisms, nevertheless a growth phase of some minutes to some hours would permit multiplication of the microorganisms, which has the direct effect that a larger amount of nucleic acids is at our disposal (this makes it possible to take advantage of the inherent delays in recovery and transfer of the air samples collected in the rooms requiring control, until the start of analysis proper). A second advantage of using culture media is that the latter can be selective for one or more given species. As a result, the use of these media can permit selective growth and therefore detection of certain pathogenic microorganisms at the expense of other microorganisms that are of no interest, and which may possibly interfere with the analysis. Thus, provision of several different cartridges can be envisaged, each being adapted to the detection of a specific species of microorganism.

The dimensions of the cartridge 10 can for example be from 8 to 16 mm for the inside diameter, preferably 12 mm. The total thickness of the layers of beads is typically between 1 and 2 mm, which corresponds to an amount of glass beads between 0.1 and 1 g, preferably 0.3 g.

The cartridge 10 is advantageously made by an injection molding technique. The material used is for example polypropylene, polystyrene, polycarbonate, cyclic cyclo-olefins (CCOs) or PMMA; polycarbonate being preferred.

The microorganism collecting device 20 is shown in FIG. 2. This device is constituted of an air collecting module, in which cartridge 10 is placed. This air collecting module is composed of an upper element 22 and a lower element 24.

Figure 4:
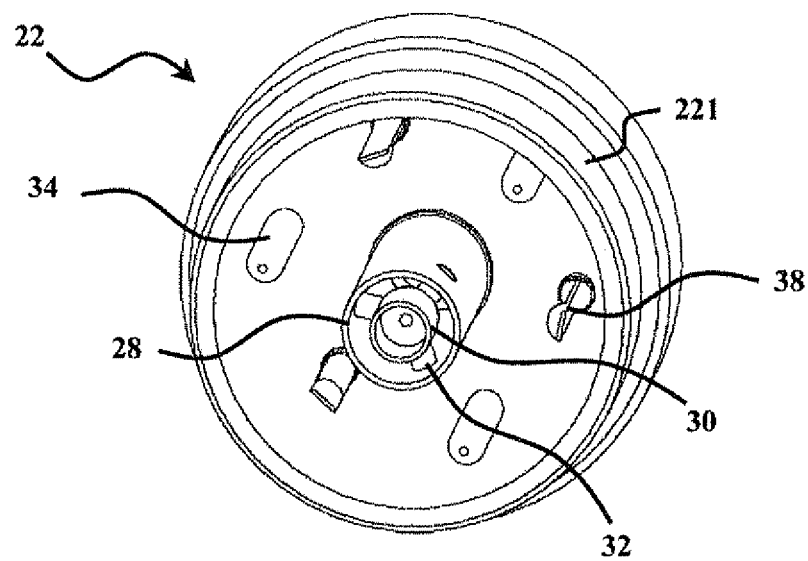
FIG. 4 shows a perspective view of the interior of the upper element of the microorganism collecting device.
Figure 5:
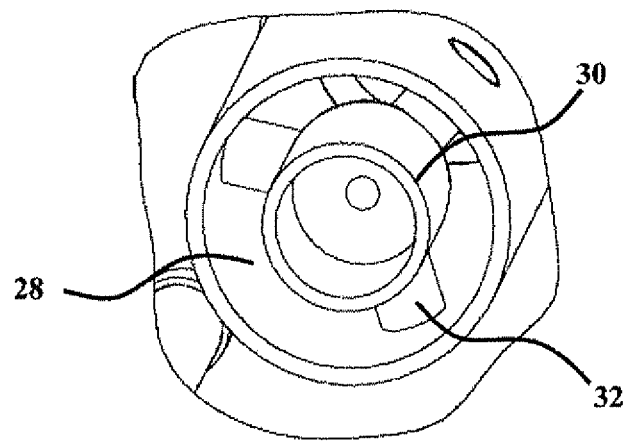
FIG. 5 shows a partial perspective view of the interior of the upper element of the microorganism collecting device as shown in FIG. 3.

The upper element 22 is of general cylindrical shape. A perspective view of it is also shown in FIGS. 4 and 5. The bottom end of this cylinder is free, whereas the top end is partially sealed by a horizontal wall 26. This wall 26 has, at its center, a hole that is extended into the upper element 22 by a duct 28. This part in fact constitutes the duct for admitting air into the air collecting module 20. According to a particular embodiment, this air admission duct can be connected to a channel of an air recycling circuit by any suitable means. An ogive-shaped cone 30 is positioned at the center of the base of this duct. This cone 30 is joined to the wall of duct 28 by blades 32. These blades 32 can be seen clearly in FIGS. 4 and 5. In the embodiment as presented in these diagrams, they are three in number. However, their number can vary. As shown in FIG. 2, the role of the assembly of cone 30-blades 32 is to create, at the base of duct 28, disturbance of the air stream entering the microorganism collecting device, so that this disturbed stream comes into contact with the jellified material of the microorganism retention zone, leading to a hollowing of the latter. This hollowing significantly improves the capture of airborne microorganisms.

As shown in FIGS. 2 and 4, the upper element 22 also has three centering pins 34 and three locking pins 38. The centering pins 34 are for ensuring proper centering of the cartridge 10 relative to the upper element 22. The locking pins 38 provide locking of the cartridge in the centered position, on the upper element 22. This is clearly shown in FIG. 2.

The upper element 22 has, in its lower part, a shoulder and a groove made on the whole perimeter of the vertical wall and intended to facilitate joining together of the upper element 22 and the lower element 24.

The lower element 24 is also of general cylindrical shape. The top end of this cylinder is free, whereas the bottom end is partially sealed, by a horizontal wall 40 having, in its central part, roughly cylindrical openings 42 for evacuation of the air. The lower element 24 further comprises a pin 44 for supporting and positioning the cartridge 10. The lower element 24 will then be positioned on the upper element 22. The cartridge 10 is again positioned, resting on the lower element 24, by means of pin 44. In fact, when cartridge 10 is placed in the bottom element 24, element 44 enters duct 12 of the cartridge, thus placing and locking the latter in the correct position.

The top end of the vertical circular wall of the lower element 24 can have, on its inside surface, a lip made on the whole perimeter of this wall. This lip is intended to interact with the shoulder and groove provided in the upper element 22 so as to provide locking between the upper element 22 and the lower element 24. Fitting together of the upper 22 and lower 24 elements is allowed by complementary shape of their lower and upper end, respectively. It is necessary for this joining together to be reversible.

An alternative means for joining together elements 22 and 24 can be joining together by screwing one element onto the other. For this purpose, the end of the wall of one of the elements 22 or 24 can have an external thread and the end of the wall of the second element a corresponding internal thread.

What is important is that the collecting means is hermetically sealed, to avoid all parasitic ingress of air.

According to a particular manner of using the air collecting means, the bottom end of the air evacuation duct 22 can be connected to an air aspirating pump (not shown) or any equivalent pumping means. This pump is used for aspirating the ambient air into the air collecting means, when for example we wish to perform an analysis of the ambient air in a particular environment, such as a hospital room, or a room for production of pharmaceuticals or foodstuffs. For this purpose, it may be preferable to have a pumping means operating autonomously and continuously.

The air collecting module, 22 and 24, can for example have an outside diameter between 10 and 40 mm, preferably 20 mm. The inside diameter of the air admission duct is for example 6 mm.

This air collecting module 10 can advantageously be made of a material that can be sterilized, in particular by autoclaving. Thus, it can be of metal, such as aluminum or steel. It can also be of polymer such as polycarbonate, cyclic cyclo-olefins (CCOs) or PMMA.

When the air circulation in the microorganism collecting device is switched on, the path followed by the air is shown by the arrows in FIG. 2. Thus, it can be seen that the air enters the microorganism collecting device by the air admission duct 28. The duct 12 of the cartridge 10 is partially inserted into the air admission duct 28, more particularly into cone 30. The air stream at the base of duct 28 is transformed, at the vertex of cone 30, into a peripheral flow. Moreover, the presence of cone 30 also prevents the air entering duct 12. As described above, a disturbed air stream arrives on the jellified material 19 (beads 18 not shown), leading at this point to retention by impact of the microorganisms transported in the air stream. This process is therefore relatively similar to what occurs in microbiological air samplers.

As for the air, it continues on its path, aspirated by the pumping means. It rises along the inside surface of the vertical wall 16 of the cartridge 10. It goes down again along the outside surface of this same wall and leaves the air collecting module 20 by the evacuation openings 42.

The air flow collected in the air collecting module 10 can be for example between 20 and 100 liters/minute (l/min). Advantageously, it is 50 l/min.

Once the stage of retention/concentration of the microorganisms within the cartridge is completed, the latter is removed from the air collecting module by detaching the upper 22 and lower 24 elements from said means, either by taking apart, or by unscrewing.

At this stage, there is an opportunity for incubating the cartridge in a stove at 37° C., if we wish to carry out culture of the microorganisms concentrated in said cartridge. As already explained above, said incubation generally lasts for some tens of minutes to some hours, so as not to prolong the analysis time excessively. However, if there is no urgency in obtaining an analysis result, incubation of the cartridge for a longer time, more in keeping with the requirements for bacterial growth, i.e. about twenty-four hours, can be envisaged.

Similarly, it can also be envisaged to store the cartridge in an environment that is suitable for said storage, such as a cold room, if we wish to postpone the analysis.

According to one embodiment of the invention, cartridge 10 can be supplied placed directly in the air collecting module. This type of presentation has the advantage that the user does not have to place the cartridge in the air collecting module, thus reducing the risk of contamination during this stage. It is particularly advantageous in this instance if the air collecting module is made of the same material as the cartridge, namely of polypropylene, polycarbonate or PMMA. Manufacture by injection molding is then particularly suitable.

Figure 6:
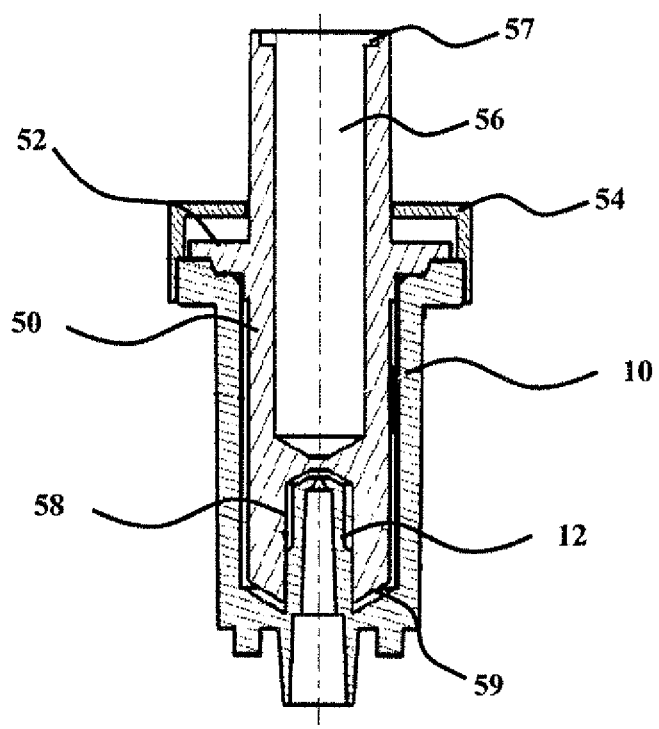
FIG. 6 shows a view in longitudinal section of the device for lysis of microorganisms.

When collection of the microorganisms, and possibly incubation, is completed, cartridge 10 is connected to a rotor 50 in order to constitute the device for lysis of microorganisms, as shown in FIG. 6. For this purpose, rotor 50 is inserted in cartridge 10 by the free end of the latter, with a vertical translational movement.

The rotor 50, shown in longitudinal section in FIG. 6, has a body of general cylindrical shape with a circular cross section. The body has, on the upper part of its outside wall, a flange 52, which has the function of ensuring that the cartridge 10-rotor 50 assembly is liquid-tight, when the rotor is fully inserted into cartridge 10, coming to rest on the top end of the vertical wall of cartridge 10.

Figure 8A:
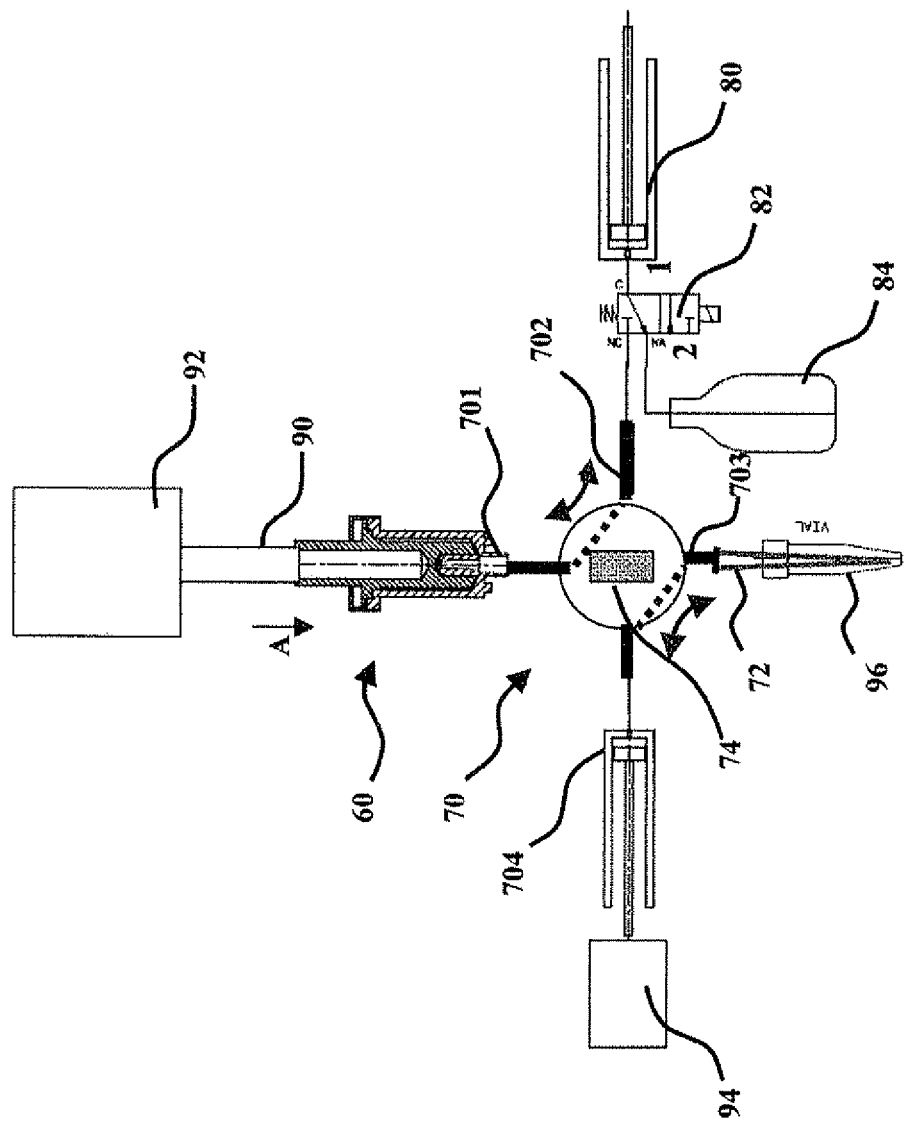
FIG. 8A shows a partial view in longitudinal section of the system for lysis of microorganisms at the level of the multi-way valve, in a first configuration of the latter.
Figure 8B:
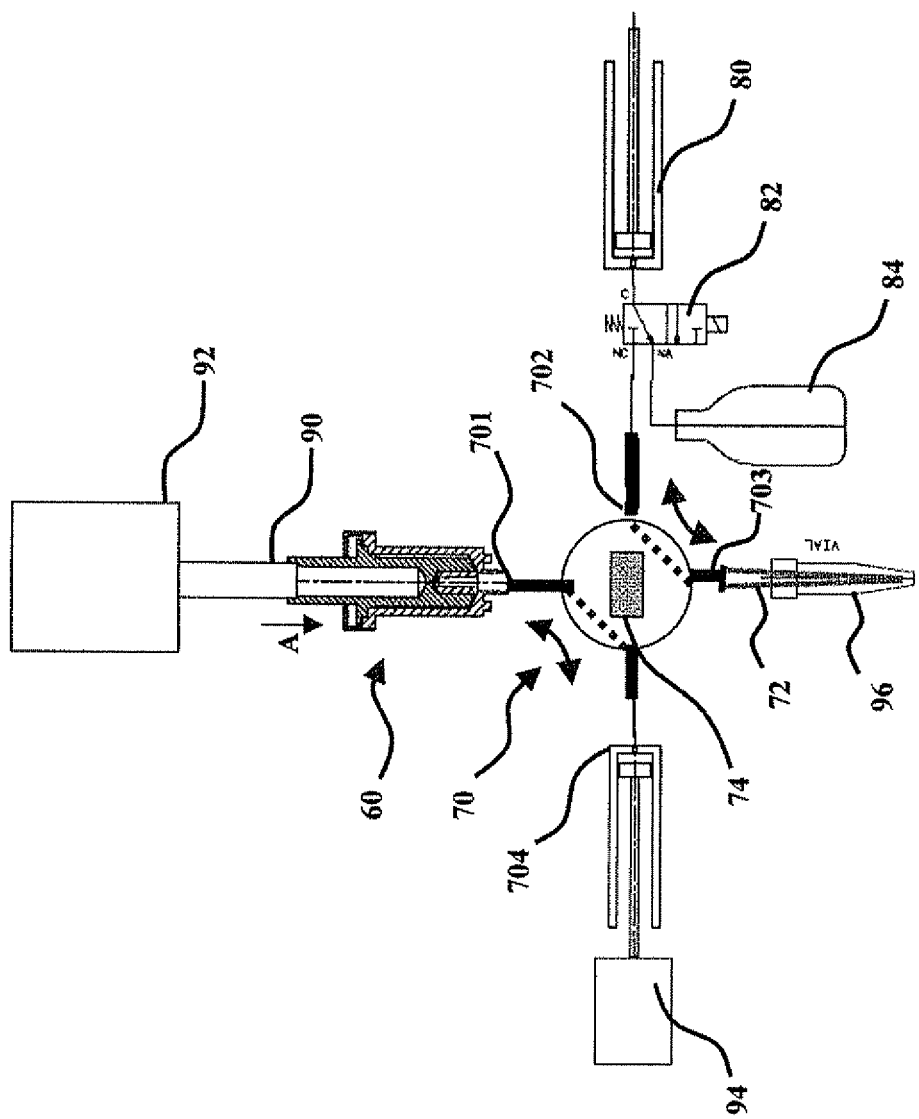
FIG. 8B shows a partial view in longitudinal section of the system for lysis of microorganisms at the level of the multi-way valve, in a second configuration of the latter.

For reinforcing the hermeticity, a cap 54 can be fixed on cartridge 10 by any suitable means so as to keep rotor 50 integral with the cartridge. For example, cap 54 can be fixed by fitting together or by screwing. The cap is of roughly annular shape and will be threaded onto the top of the rotor constituting the blind duct 56, provided in the rotor. At the top end of this blind duct, two diametrically opposite grooves 57 are made in the wall. These grooves have the function of receiving the end of a transmission shaft 90 of a means 92 for rotating said rotor, as shown in FIGS. 8A and 8B. The end of this shaft thus has a shape complementary to these grooves, in the form of a rib which will be inserted in these grooves. The drive shaft can be that of an electric motor. Alternatively, it can be a part of a device for manual rotation.

As shown in FIG. 6, rotor 50 has, in its lower part, external shapes that are perfectly complementary to the internal shapes of cartridge 10. As a result, rotor 50 will be perfectly positioned inside cartridge 10, with duct 12 performing the role of a guide, by being inserted in a cavity 58 provided at the base of the rotor 50. This cavity 58 is of roughly cylindrical shape with a circular cross section and its top end is of roughly conical shape. Rotor 50 is positioned until its bottom wall 59 rests on the assembly constituted of the beads 18 and the jellified material 19.

The rotor 50 and the cap 54 are advantageously made of the same polymer material as the cartridge, namely of polypropylene, polycarbonate or PMMA. Preferably, these parts are made by injection molding of transparent polycarbonate (Makrolon® 2858, Bayer).

The cartridge 10—rotor 50—cap 54 assembly therefore constitutes the device for lysis of microorganisms 60 according to the invention and will be called "lysis device" hereinafter.

Figure 7:
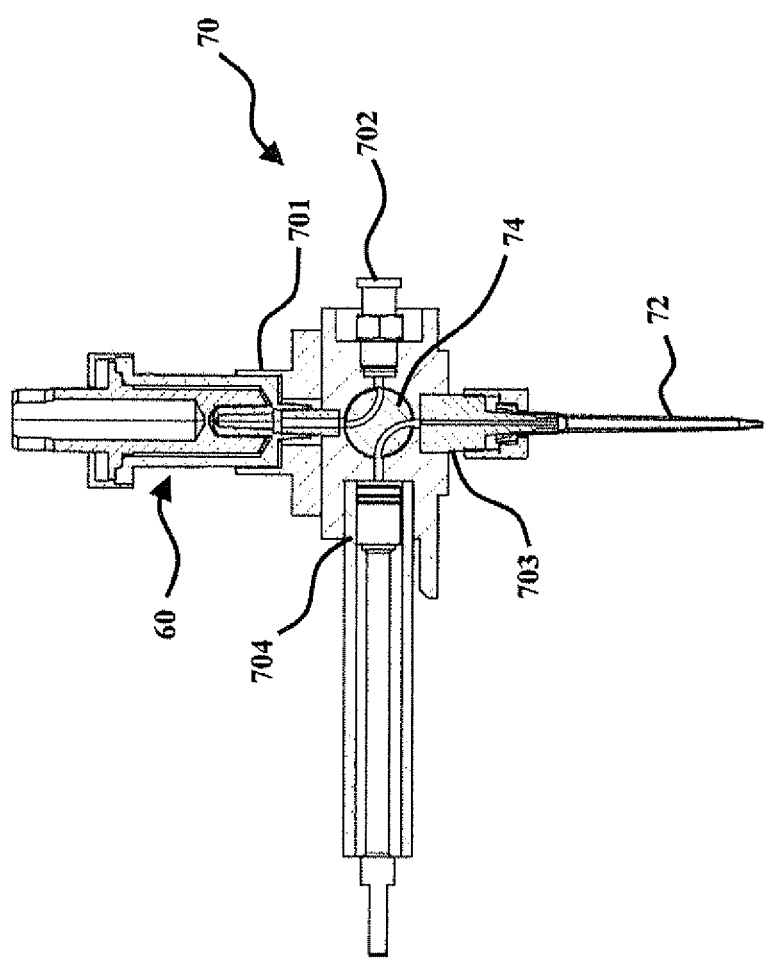
FIG. 7 shows a view in longitudinal section of the assembly constituted of the device for lysis of microorganisms and the multi-way valve.

Once the lysis device is constructed, it is placed on a 4-way valve, as shown in FIG. 7. This valve 70 has the first way 701 intended for receiving the lysis device 60. Said device is connected on the valve by the base of duct 12 of cartridge 10. The second way has a connecting hole 702, intended to be connected to a first aspiration-expulsion means, part of the system for lysis of microorganisms and purification of nucleic acids, according to the invention. Advantageously, this aspiration-expulsion means is a pump, also connected to the container containing the solution of elution buffer. Said pump is shown schematically in FIGS. 8A and 8B. Its operation will be explained below. The third way has a connecting hole 703 on which a disposable cone 72 is fixed. Finally, the fourth way is constituted of a second aspiration-expulsion means 704. This second means is a syringe which is integral with the valve. This syringe 704 is intended to interact with a means for translational actuation forming part of the system for lysis of microorganisms and purification of nucleic acids according to the invention and intended for moving the piston of said syringe. Finally, valve 70 has a central shaft 74 having two fluidic channels. As shown in FIG. 7, these two channels provide connection respectively between, on the one hand, the lysis device 60 and the connecting hole 702, and on the other hand, between syringe 704 and the connecting hole 703 on which the disposable cone 72 is fixed. The shaft 74 can be rotated a quarter-turn, so that the fluidic connections are changed. Connecting hole 702 is then connected to connecting hole 703 and the lysis device 60 is then connected to syringe 704.

The assembly constituted of the lysis device 60 and valve 70 constitutes the consumable part. It is then placed on the system for lysis of microorganisms and purification of nucleic acids. It is an automatic system having three separate main functions: a lysis function, a liquid transfer function and a purification function. These functions are described below.

The lysis device 60-valve 70 assembly is placed in the system for lysis of microorganisms and purification of nucleic acids in the following way. Firstly, there is a dedicated location for fitting this assembly. This location is characterized in that it has means for fixing the valve 70. These means can for example be constituted of arms or jaws, between which the valve is inserted with force.

Once the lysis device 60-valve 70 assembly is in position, the various connections are made to the valve. This is shown schematically in FIGS. 8A and 8B. Thus, the first connection is made by the connecting hole 702 of valve 70. It is a final connection to the aspiration-expulsion means 80 which is on the automatic system permanently, connected to the connecting hole 702. As explained above, this aspiration-expulsion means 80 is preferably in the form of a fixed pump, an integral part of the automatic system, not shown in full in FIGS. 8A and 8B. More precisely, pump 80 is in fact connected to a valve 82, also placed permanently on the automatic system. This fixed valve 82 is moreover in fluidic connection, on the one hand with valve 70 via connecting hole 702, and on the other hand with a reservoir 84 containing a so-called elution buffer. The fixed valve 82 thus makes it possible to connect the fixed pump 80, either to valve 70, or to reservoir 84, depending on its position.

The lysis device-valve assembly is also connected to the transmission shaft 90 of means 92 for rotating the rotor of the lysis device. It should be noted that once this connection is made, transmission shaft 90 exerts a pressure on the rotor along a vertical component according to arrow A on FIG. 8A, so that this pressure is transmitted from the rotor onto the assembly constituted of the beads 18 and the jellified material 19.

The third connection between the lysis device-valve assembly and the automatic system consists of the connection between syringe 704 of valve 70 and the actuating means 94 of said syringe. This actuating means is a means for translational actuation, such as an assembly constituted of a stepping motor and an endless screw and makes it possible either to pull, or to push the piston of the syringe 704, and thus, either to aspirate a liquid into the syringe, or to expel a liquid contained in the syringe.

Finally, the fourth connection between the lysis device-valve assembly and the automatic system concerns the means for rotational actuation of shaft 74 of valve 70. This means is not shown in FIGS. 8A and 8B. It is a motor that is able to cause a transmission shaft to rotate, said transmission shaft being connected to shaft 74 of valve 70.

During application of the protocol for lysis of the microorganisms collected in cartridge 10, valve 70 is configured in such a way that the lysis device 60 is in fluidic connection with the assembly constituted of pump 80 and the fixed valve 82. The syringe 704 is then in fluidic connection with connecting hole 703, on which the disposable cone is fixed. The fixed valve 82 is initially configured in such a way that pump 80 is in fluidic connection with the elution buffer reservoir 84. Pump 80 then aspirates a predetermined amount of elution buffer. The configuration of fixed valve 82 is then changed so that pump 80 becomes connected fluidically to the lysis device 60 via valve 70. Pump 80 then expels the volume of elution buffer taken up, which travels into the lysis device 60 and more particularly into the interstitial space between the inside wall of cartridge 10 and the outside wall of the rotor 50 (cf. FIG. 6). The elution buffer then wets the jellified material 19 and the beads 18. The jellified material 19 is then dissolved by the combined action of the elution buffer and slow rotation of the rotor 50. The beads are then in suspension in the latter. This operation of suspension, combined with the effect of pressure exerted by the rotor and the rotation of the latter, leads to displacement of a fraction of the beads 18 into the interstitial space between the inside vertical wall of cartridge 10 and the outside vertical wall of the rotor 50. It should be noted that this interstitial space preferably has a width between 600 and 800 µm. This width is directly related to the diameter of the beads 18 used. In fact, the beads must, simultaneously, be able to circulate easily in this space and be able to be rotated by rotating the rotor 50. For this purpose, the vertical outside wall of the rotor can have a rough surface, which facilitates rotating the beads.

Once the beads are distributed in the retention zone of the cartridge and along the vertical wall of the rotor, the latter can then be fully inserted in the cartridge.

Of course, the microorganisms retained both on the jellified material and on the beads are transferred into the interstitial space in the same way as the beads 18, by the stream of elution buffer.

Once the beads 18 are distributed along the vertical outside wall of the rotor 50, the lysis stage proper is initiated. The rotor 50 is then caused to rotate by the rotating means/motor 92 and by means of the transmission shaft 90. Nevertheless, it is possible to envisage rotating the rotor manually, in a simplified protocol not using the system for lysis of microorganisms and purification of nucleic acids.

As an example, the values for the rotary speed can be between 200 and 3000 rev/min. Preferably, the rotor is initially rotated at a slow speed of 200 rev/min for purposes of distribution and homogenization of the beads and the elution buffer in the interstitial space. This slow rotation lasts about 15 seconds.

Then the rotary speed increases, reaching a value between 1000 and 3000 rev/min for a time between 1 and 5 minutes. It is during this period that lysis of any microorganisms collected from the air is carried out.

It is quite clear that the choice of speed and time of rotation of the rotor depends on the type of microorganisms that are to be lysed.

During this stage, beads 18 are rotated about their axis of symmetry by friction against the vertical external surface of the rotor and the vertical internal surface of the cartridge. This double rotation leads to mechanical lysis of the microorganisms that are trapped between the beads 18 and the respective surfaces of the rotor or of the cartridge. This results in release of the nucleic acids into the elution buffer.

Once the lysis stage is completed and the nucleic acids have been released, the elution buffer containing the nucleic acids must be aspirated. Valve 70 then changes its configuration by rotating its shaft 74, so that the lysis device 60 and syringe 704 are again in fluidic communication, as shown in FIG. 8B. The piston of the syringe 704 is then moved in translation by the actuating means 94, in order to aspirate the elution buffer containing the nucleic acids into said syringe 704. This aspiration stage takes place while rotor 50 is still being rotated, but at low speed (about 200 rev/min).

Valve 70 then goes back to its initial configuration, as shown in FIG. 8A, so that syringe 704 is in fluidic communication with the connecting hole 703. The elution buffer containing the nucleic acids is then ready to be dispensed in a tube via cone 72, for purposes of purification of said nucleic acids. In fact, the lysate contained in the elution buffer does effectively contain the nucleic acids, but also all the cellular debris.

To do this, an analysis tube 96 is brought close to cone 72. Advantageously, the automatic system has a holder for receiving said tube. In this case, said holder can be connected to an arm which can be moved between a bottom position or position of rest, in which the tube can be inserted in the holder, and a top position or working position in which the tube is near cone 72 (as shown in FIGS. 8A and 8B). Of course, it is preferable for cone 72 to go into tube 96. Tube 96 has a so-called lysis buffer and magnetic silica particles, required for purification of the nucleic acids. These particles have a diameter between 1 and 3 µm. Moreover, a pre-pierced septum (not shown) is placed on the orifice of tube 96 in order to avoid any contamination of the latter. As tube 96 rises, cone 72 passes through the septum by the pre-pierced hole. The elution buffer with the lysate is then dispensed in the analysis tube. At this stage, it is preferable to use syringe 704 to perform several aspirations/expulsions, in order to homogenize the lysate with the lysis buffer and the magnetic particles. The function of the lysis buffer is to stabilize the nucleic acids (protection against nucleases) and to adjust the pH to an optimal value for the capture phase.

If the mixture is correctly homogenized, the tube can then be left at rest to permit passive capture of the nucleic acids by the magnetic particles. The time at rest can be for example 2 minutes. In the case when homogenization is not correct or in the absence of homogenization, capture of the nucleic acids will be performed actively. In fact, the tube and the magnetic particles that it contains will be submitted to magnetic fields of different orientations. To do this, the tube is placed in the bottom position and then is brought into contact with the magnets via the arm carrying it. These magnets can be positioned on two parallel plates integral with the arm carrying the tube. These two plates are movable in horizontal translation by means of an ad hoc displacement means and are thus displaced so that the tube is then between said plates. The number of magnets on each plate is variable. It is advantageous for the magnets to be at different heights on the plates. Moreover, it is important that the magnets on one plate are not placed opposite the magnets on the other plate, but are offset relative to the direction of displacement of the tube according to a defined sequence. Thus, during displacement of the plates, the tube is submitted progressively either to the magnetic field of a magnet on the first plate, or to the magnetic field of a magnet on the second plate. These fields can be positioned at a different height relative to the trajectory of the plates. As a result, the magnetic particles, being attracted by these magnets, form a cluster, and this cluster is caused to move in the tube, as a function of the attraction exerted by the magnets and especially their position relative to the tube. It should be noted that this relative positioning of the magnets relative to the analysis tube can also be obtained by displacement of the tube along a vertical axis; in which case, the magnets are all placed at the same height and according to a defined sequence. In the case of active capture of the nucleic acids, the time dedicated to said capture will be longer (between 4 and 6 minutes).

Once capture of the nucleic acids has been effected, one or more successive stages of washing are applied. For this purpose, the tube is placed opposite a magnet in a high position so as to accumulate the magnetic particles carrying the nucleic acids in the top part of the tube against the vertical wall. The tube is then moved to a high position so that cone 72 comes into contact with the liquid contained in the tube. The liquid contained in the tube is then aspirated into syringe 704 by actuating its piston. Syringe 704 then serves as a storage container for the liquid wastes aspirated in the tube. In order to begin washing of the nucleic acids, valve 74 is put in the configuration in which the connecting hole 702, and therefore the pump 80, is in fluidic communication with connecting hole 703. Valve 82 is put in the position allowing aspiration of elution buffer by pump 80. The volume of elution buffer aspirated is for example 300 µl. The position of valve 82 is then changed to enable pump 80 to dispense the elution buffer in tube 96. To ensure optimal washing, the tube is returned to the low position and the plates carrying the magnets are moved again in order to optimize the exchanges between the particles and the elution buffer. The plates are able to effect several reciprocating movements, at a variable speed depending on requirements. The elution buffer contained in the tube is then aspirated by means of the syringe 704, as described above. New washing stages can optionally be performed in an identical manner. It should be noted that the piston of the syringe 704 is actuated in stages, so that syringe 704 is gradually filled with the liquid aspirated in the analysis tube, whether it is lysis buffer or elution buffer used for the washings. Once the nucleic acids have been transferred to the analysis tube, syringe 704 is then only assigned to the role of storage of liquid wastes, which represents a considerable advantage. Moreover, it should be noted that pump 80 only serves for dispensing elution buffer and is never in contact with "contaminated" matter. This aspect is also particularly important, since pump 80 and valve 82 remain permanently on the automatic system, in contrast to syringe 704 which is an integral part of valve 74, which is intended for single use.

Once the washings of the nucleic acids have been performed, the last aspiration of the elution buffer in tube 72 is only partial. In fact, a defined volume of elution buffer is kept in the tube and constitutes the elution volume in which the nucleic acids will be eluted, i.e. dissociated from the magnetic particles. The elution volume can vary between 5 and 150 µl, and is preferably 25 or 40 µl. For this final aspiration, a cluster of magnetic particles is formed at the bottom of the tube, by putting the latter opposite a magnet in the low position. In contrast, aspiration is effected from the surface of the liquid, to avoid any aspiration of particles.

In the volume that remains, elution of the nucleic acids is then undertaken. To do this, the tube is heated to 75° C. by a heating module, integral with the tube holder, until a temperature of 65° C. is reached in the liquid for about 5 min. Simultaneously with the heating stage, the tube is submitted to the magnets situated in the low position, to promote elution.

Once the nucleic acids have been purified and eluted in the elution volume, they can be amplified for purposes of analysis. For this, some or all of the elution volume must be brought in contact with the so-called conditioning buffer for amplification (40 mM Tris HCl, pH 8.5, 12 mM $MgCl_2$, 70 mM KCl, 5 mM dithiothreitol, 15% v/v DMSO, 1 mM of dNTP, 2 mM of each NTP, 0.2 µM of primers, 0.1 µM of molecular beacons. This contacting can be effected according to two different protocols depending on the functionalities available on the automatic system.

According to a first protocol, elution and conditioning for amplification are performed in two different tubes. In this case it is necessary to take, from the analysis tube, a predetermined fraction of the elution volume containing the purified nucleic acids. This fraction is then dispensed in a second tube in which conditioning for amplification will be carried out, and which already contains the required amount of buffer for conditioning for amplification. This tube will then be transferred to the instrument in which amplification of the nucleic acids will take place. The fraction of the reaction volume is then taken by means of the fixed pump 80. In this case, valves 70 and 82 will have been configured so as to permit fluidic communication between pump 80 and the connecting hole 703. The analysis tube is placed in the high position so that the cone is immersed in the elution volume. The fraction is then aspirated by pump 80. It will be recalled that this pump 80, and more generally the fluidic circuit borrowed by the fraction of elution volume taken, have only been in contact, throughout the protocol for lysis and purification, with the elution buffer. Therefore there is no possibility of contamination of the fraction that will be used for amplification of the nucleic acids. Once this fraction has been taken, the analysis tube can be replaced with the tube for conditioning for amplification. For this purpose, the analysis tube is brought down to the low position, so that it can be withdrawn from the holder and the tube for conditioning for amplification can be put in place. This tube is then raised to the high position so that the cone goes into the tube and the fraction of elution volume is then dispensed by pump 80.

Alternatively, the automatic system can be provided with a specific module for management and conveying of the tube for conditioning for amplification.

This first protocol offers the advantage that contact between the silica particles and the buffer for conditioning for amplification is avoided. It is known, in fact, that such particles can inhibit reactions of amplification of nucleic acids.

According to a second protocol, the buffer for conditioning for amplification and the elution volume are brought in contact directly in the analysis tube, and in this case the buffer for conditioning for amplification is added to the analysis tube. Said addition can be performed manually or automatically. In this case, the automatic system must be permanently equipped with a second dispensing system, namely a container containing the buffer for conditioning for amplification, a syringe for aspiration and expulsion of said buffer, a valve equivalent to valve 82 and a needle or cone that can pass through the septum fitted on the analysis tube.

Regardless of the protocol used, it may be advantageous to remove the cluster of silica particles to the outside either of the elution volume alone, or of the mixture of elution volume and buffer for conditioning for amplification contained in the analysis tube, before taking the fraction that will finally serve for amplification. This can be done by submitting the tube to magnetization by a magnet situated in the high position.

Moreover, all of the systems and devices according to the invention, described above, are suitable for permitting complete traceability throughout the protocols for lysis of microorganisms and purification of nucleic acids. In fact, firstly, all the consumables (cartridge, rotor, multi-way valve, tubes) are identified with ad hoc means of identification (1D or 2D barcodes, RFID tags, etc.). Moreover, in the case when the microorganisms are collected by an air aspirating means, the latter must be able to have a wireless communication means, enabling it to communicate with the system for lysis of microorganisms and purification of nucleic acids. Said wireless communication means are for example WiFi (standard 802.11b), Bluetooth (standard 802.15) or ZigBee (standard 802.15.4) systems. The data that can be transferred via these wireless connection systems can relate for example to the places (collection room/point), the sampling conditions (time, flow rate, hygrometry, temperature, atmospheric pressure), identification of the operator and of course the elements identifying the consumables.

The device and systems according to the invention are also entirely suitable for analysis of clinical samples, such as samples from whole blood or from tissue biopsies. In this case, the cartridge is used without the air collecting module. In the case of a liquid sample such as whole blood, the latter is placed in the cartridge and then the latter is combined with the rotor in the cap for constituting the device for lysis of microorganisms. The latter is then placed in the automatic system, for lysis of the microorganisms and recovery of the nucleic acids. In the case of tissue biopsies, the latter are first cut into slices of a few millimeters and then placed in the cartridge, which is then combined with the rotor in the cap for constituting the device for lysis of microorganisms. The latter is then placed in the automatic system, for lysis of the cells and recovery of the nucleic acids.

EXAMPLES

Example 1

Reference Protocol

Preparation of Consumables:
Preparation of the cartridge:
The cartridge is filled with a predetermined amount of glass beads and agarose gel:
    0.3 to 0.45 g of glass beads (diameter: 420-600 µm)
    Composition of the gel: 1% agarose-1% glycerol
The volume of elution buffer used for performing the lysis of microorganisms is 300 µl.
Preparation of the analysis tube:
The analysis tube placed in the automatic system and intended for recovering the lysate is filled with 30 µl of magnetic silica particles and 200 µl of lysis buffer (guanidinium thiocyanate).
Lysis Parameters:
    Lysis time: 4 minutes
    Rotary speed of the rotor: 200 rev/min (low speed); 2000 rev/min (high speed)

Lysis Parameters:
Aspiration of the lysate from the cartridge into the syringe of the multi-way valve:
    Volume of aspiration of the syringe=1000 µl
    Rate of aspiration of the syringe=70 mms-1
    Time of rotation of the rotor during aspiration=9 s
    Rotary speed of the rotor during aspiration=200 rpm
Dispensing of the Lysate from the Syringe of the Multi-Way Valve to the Analysis Tube:
    Volume of aspiration from the syringe of the multi-way valve=1000 µl
    Rate of aspiration of the syringe=70 mms-1
Parameters for Purification of the Nucleic Acids:
Purification comprises 3 stages:
    isolation of the nucleic acids
    washing with elution buffer (3 times)
    elution in elution buffer (pH 8.5)
After transferring the lysate to the analysis tube (0.5 ml), the latter contains 30 µl of silica beads, 200 µl of lysis buffer and 120-150 µl of lysate.
Two types of oscillations of the silica particles are applied by means of the magnets:
    High oscillations which are produced between the magnets in the high position
    Low oscillations which are produced between the magnets in the low position
The high oscillations are used for effecting the capture of the nucleic acids by the magnetic particles, but also for the washing stages (removal of supernatant). The low oscillations are used for the elution stage and are combined with heating of the tube.
Parameters for Capture of the Nucleic Acids:
    Rate of oscillation=5 mms$^{-1}$
    Number of oscillations=112
    Oscillation amplitude=27 mms$^{-1}$
Parameters for Washing:
    Rate of oscillation=5 mms$^{-1}$
    Number of oscillations=10
    Oscillation amplitude=27 mms$^{-1}$
Parameters for Removal of Supernatant:
    Aspiration by the syringe of the multi-way valve=600 µl
    Pump speed=100 mms$^{-1}$
Parameters for Distribution of the Elution Buffer by the Pump Fixed in the Analysis Tube:
    Volume of distribution=400 µl
    Pump speed=100 mms$^{-1}$
Parameters for Elution:
    Rate of oscillation=50 mms$^{-1}$
    Amplitude of oscillation=9 mms$^{-1}$
    Target temperature=75° C.
    Heating time=300 s
    Volume of elution buffer=45 µl

Example 2

Mechanical Lysis of Tissues

A study was conducted to evaluate the performance of mechanical lysis in the lysis device according to the invention for the purpose of disrupting the walls of living cells of microorganisms to release the tRNAs. These tests were conducted on solid tumor samples.
Protocol Elaborated and Tested:
Reagents & equipment:
    Breast cancer tumors, pre-defatted and stabilized with the RNAlater® equipment marketed by Qiagen,
    Petri dishes,
    Sterile 2 mL tubes, Plastic tweezers and disposable scalpels, Lysis devices according to the invention (cartridge and rotor) decontaminated with Actril, Glass beads of 400-600 μm, RNeasy Plus kit marketed by Qiagen+Qiacube automatic extraction system.

Preparation:

Clean the bench and the pipets with RNAse Zap before beginning extraction,

Leave the tumors, frozen at −80° C., to thaw,

Deposit the tumor in a Petri dish, avoiding taking RNAlater®,

Wash twice with 300 μl of RLT buffer (Qiagen) to remove residual RNAlater.

Grinding the tumors:

Cut up the tumor finely (diameter about 4 mm) with the scalpel,

Recover the pieces of tumor using plastic tweezers and transfer to a 2 mL tube containing 300 μL of RLT (+3 μL of β-mercaptoethanol), Grind the pieces of tumor with:

Qiagen Tissue Ruptor: speed 2 for 2 minutes, or the device for lysis of microorganisms according to the invention: 0.4-0.5 g of glass beads (400-600 μm), 2000 rev/min, 2×20 seconds.

Recover the sample and adjust the volume with RLT buffer to have a volume of 300 μL before purification.

Purification of the tRNAs with the Qiagen RNeasy Plus Mini kit:

1. Put the 300 μL of RLT buffer recovered after grinding without the remaining tumor debris in a 2 mL tube, 2. Prepare the 2 types of columns for purification and fixation of RNAs: column gDNA Eliminator and RNA spin, 3. Prepare the buffers, the Qiagen extraction shuttles and the elution tubes, 4. Prepare the Qiacube tester following the robot's instructions and start the run, 5. Recover the 80 μl of eluate and freeze the purified tRNAs at −80° C., 6. Dosage: 1 μL of undiluted eluate per Nanodrop, 7. Measurement of quality of the extracted tRNA: analysis of quality is performed according to protocol RNA 6000 Nano on Agilent bioanalyzer.

Just as in conventional electrophoresis, distribution of the transcripts is observed, with two main peaks for 18 s and 28 s rRNA.

Results:

Two biopsies were used for this study, all prepared and stored identically. These biopsies are circular, with a diameter of about 4 mm and a thickness of 1.5 mm. Their mass is evaluated at around 10 mg. These biopsies were roughly divided into two in order to carry out the two types of mechanical lysis in parallel (reference lysis Tissue Ruptor and PPM). However it should be noted that the amount of tissue used is not identical from one test to another, the aim being to ensure proper execution of the test, rather than a comparison of performance between the reference technique and the protocol according to the invention.

Analysis of purity is based on the ratio between absorbance values at different wavelengths: 260 nm for nucleic acids, 230 nm for salts and 280 nm for proteins. A value of the ratio close to 2 reflects good purity of the nucleic acids.

| Biopsy | Extraction Protocol | | tRNA | Purity | |
| --- | --- | --- | --- | --- | --- |
| | Lysis | Purification | (ng/μl) | 260/280 | 260/230 |
| 1 | Tissue Ruptor (Qiagen) 2 min, speed 2 | Kit: RNeasy Plus Robot: Qiacube | 3.4 | 0.86 | 0.19 |
| 1 | Device according to the invention 2 × 20 s at 2000 rev/min 0.4 g of beads 420-600 μm | Kit: RNeasy Plus Robot: Qiacube | 2.2 | 0.42 | 0.11 |
| 2 | Tissue Ruptor from Qiagen 2 min, speed 2 | Kit: RNeasy Plus Robot: Qiacube | 31.7 | 2.09 | 0.56 |
| 2 | Device according to the invention 2 × 20 s at 2000 rev/min 0.4 g of beads 420-600 μm | Kit: RNeasy Plus Robot: Qiacube | 81.1 | 2.10 | 1.70 |

In the case of biopsy 1, it can be seen that the amount of tRNA extracted is very small. This can be explained by the fact that the biopsy underwent degradation, leading to a loss of material.

In the case of biopsy 2, it can be seen that a significant amount of tRNA was extracted by both techniques. Moreover, it can be seen that the purity is good.

It is thus clear from these examples that the device according to the invention offers good performance for collecting the bacteria contained in a sample of air, lysing them and providing recovery of the nucleic acids from said bacteria for purposes of analysis. For this, the device employed will be constituted firstly of a cartridge inserted in the air collecting module and, secondly, of the cartridge containing the bacteria collected, combined with means for recovery of the nucleic acids.

The invention claimed is:

1. A device for collecting airborne microorganisms, the device comprising:
    an air collecting module, wherein the air collecting module comprises:
    i) an upper element having an air admission duct permitting entry of an air stream into the module, the duct comprising means for disturbance of the air stream at its base,
    ii) a lower element having means for evacuation of the air stream, permitting the air stream to exit, wherein
    the upper and lower elements can be made integral with one another so that the air stream can be created within the air collecting module; and
    a cartridge, wherein the cartridge has a roughly cylindrical shape and has a microorganism retention zone, the microorganism retention zone having means for lysis of microorganisms, and the cartridge is positioned within the air collecting module, and wherein the means for disturbance of the air stream comprises an ogive-shaped cone positioned at the center of a bore of the air admission duct and at least one blade connecting the ogive-shaped cone to an inside surface of the air admission duct.

2. The device as claimed in claim 1, wherein the microorganism retention zone of the cartridge further comprises a material that is able to retain the microorganisms, to hold the means for lysis in place, and to be dissolved in the presence of a liquid.

3. The device as claimed in claim 1, wherein the air collecting module is connected to an air recycling circuit or to an air aspirating device.

4. A method of collecting airborne microorganisms, the method comprising steps of:
   a) [placing the cartridge as claimed in claim 1 inside the air collecting module as claimed in claim 1, so as to obtain the microorganism collecting ] obtaining the device for collecting airborne microorganisms as claimed in claim 1 by placing the cartridge as claimed in claim 1 inside the air collecting module as claimed in claim 1, the microorganism retention zone within the cartridge being in communication with the air admission duct of the air collecting module,
   b) causing air to go into the air collecting module, and
   c) collecting the airborne microorganisms in the microorganism retention zone of the cartridge.

5. A method of lysis of airborne microorganisms, the method comprising steps of:
   a) [placing the cartridge as claimed in claim 1 inside the air collecting module as claimed in claim 1, so as to obtain the microorganism collecting ] obtaining the device for collecting airborne microorganisms as claimed in claim 1 by placing the cartridge as claimed in claim 1 inside the air collecting module as claimed in claim 1, the microorganism retention zone within the cartridge being in communication with the air admission duct of the air collecting module,
   b) causing air to go into the air collecting module,
   c) collecting the airborne microorganisms in the microorganism retention zone of the cartridge,
   d) removing the cartridge from the air collecting module,
   e) placing a rotor in the cartridge, [so as to obtain] thereby obtaining a device for lysis of microorganisms, the device comprising:
      the cartridge, wherein the cartridge has a roughly cylindrical shape [,] and has a microorganism retention zone, and the cartridge performs the role of stator; and the rotor, wherein the rotor comprises a rotating means,
   f) positioning the device for lysis of microorganisms in a system for lysis of microorganisms and purification of nucleic acids, the system comprising:
      means for positioning the device for lysis of microorganisms;
      means for rotating the rotor when the device for lysis of microorganisms is placed on the [positioning ] means for positioning the device for lysis of microorganisms;
      at least one container for receiving the nucleic acids;
      at least one means for aspiration/discharge of liquid;
      a multi-way valve, wherein the multi-way valve is in fluidic communication with the device for lysis of microorganisms, the container for receiving purified nucleic acids and the means for aspiration/discharge of liquid,
   g) introducing an elution liquid into the cartridge, wherein the elution liquid suspends the [lysis] means for lysis of microorganisms as claimed in claim 1, the [lysis] means for lysis of microorganisms being situated in the microorganism retention zone of the cartridge, and
   h) mechanically lysing the microorganisms, by rotating the rotor within the cartridge by the rotating means of the rotor, the rotor causing the means for lysis of microorganisms to rotate.

6. A method of extracting nucleic acids from airborne microorganisms, the method comprising [stages] steps of:
   a) [placing the cartridge as claimed in claim 1 inside the air collecting module as claimed in claim 1, so as to obtain the microorganism collecting] obtaining the device for collecting airborne microorganisms as claimed in claim 1 by placing the cartridge as claimed in claim 1 inside the air collecting module as claimed in claim 1, the retention zone within the cartridge being in communication with the air admission duct of the air collecting module,
   b) causing air to go into the air collecting module,
   c) collecting the airborne microorganisms in the microorganism retention zone of the cartridge,
   d) removing the cartridge from the air collecting module,
   e) placing a rotor in the cartridge, [so as to obtain] thereby obtaining a device for lysis of microorganisms, the device comprising:
      the cartridge, wherein the cartridge has a roughly cylindrical shape [,] and has a microorganism retention zone, and the cartridge performs the role of stator; and the rotor wherein the rotor comprises a rotating means,
   f) introducing an elution liquid [in] into the cartridge by an aspiration-discharge means, wherein the elution liquid suspends the means for [lysis] means for lysis of microorganisms as claimed in claim 1 [that is contained] in the cartridge,
   g) mechanically lysing the microorganisms by rotating the rotor within the cartridge by the rotating means of the rotor, the rotor causing the [lysis] means for lysis of microorganisms to rotate, thereby obtaining elution liquid containing the nucleic acids of the microorganisms,
   h) aspirating [the] elution liquid containing the nucleic acids of the microorganisms, [released during lysis ], and
   i) dispensing the elution liquid containing the nucleic acids of the microorganisms in a container [for receiving and purification of], thereby extracting the nucleic acids of the microorganisms.

7. The method as claimed in claim 6, further comprising an additional [stage] step of washing [and purification of] the nucleic acids extracted from step i).

8. The method as claimed in claim 4, further comprising an additional [stage] step d') wherein [stage] said step d') comprises growing the microorganisms collected in the microorganism retention zone of the cartridge.

9. The method as claimed in claim 8, [in which the ] wherein said growing the microorganisms is achieved by incubation of the cartridge in a stove for [a time in the range from]2 to 24 hours.

10. The method as claimed in claim 6, [in which staged] steps f) to i) are employed in a system for lysis of microorganisms and purification of nucleic acids, the system comprising:
    means for positioning [a] the device for lysis of microorganisms,
    means for rotating the rotor when the device for lysis is placed on the [positioning] means for positioning the device for lysis of microorganisms;
    at least one container for receiving the nucleic acids;
    [at least one ] the means for aspiration/discharge of liquid;
    a multi-way valve, wherein the multi-way valve is in fluidic communication with the device for lysis of microorganisms, the container for receiving [purified] the nucleic acids and the means for aspiration/discharge of liquid.

* * * * *